(12) United States Patent
Kawasaki et al.

(10) Patent No.: US 7,947,505 B2
(45) Date of Patent: May 24, 2011

(54) METHOD FOR TESTING EFFICACY OF ANTITHROMBOTIC AGENT

(75) Inventors: Jun Kawasaki, Tokyo (JP); Kenichi Tanaka, Kanagawa (JP)

(73) Assignees: Jun Kawasaki (JP); Kenichi Tanaka (JP)

( * ) Notice: Subject to any disclaimer, the term of this patent is extended or adjusted under 35 U.S.C. 154(b) by 218 days.

(21) Appl. No.: 11/915,273

(22) PCT Filed: Nov. 8, 2005

(86) PCT No.: PCT/JP2005/020421
§ 371 (c)(1),
(2), (4) Date: Feb. 3, 2009

(87) PCT Pub. No.: WO2006/126290
PCT Pub. Date: Nov. 30, 2006

(65) Prior Publication Data
US 2009/0280570 A1    Nov. 12, 2009

(30) Foreign Application Priority Data

May 23, 2005  (JP) ................................ 2005-149183

(51) Int. Cl.
  *G01N 33/86* (2006.01)
(52) U.S. Cl. .............. 436/69; 436/63; 422/73; 600/369; 73/61.41; 435/13
(58) Field of Classification Search .................... 436/63, 436/69; 422/73; 600/369; 73/61.41; 435/2, 435/13
See application file for complete search history.

(56) References Cited

U.S. PATENT DOCUMENTS
6,613,573 B1 * 9/2003 Cohen ............................ 436/69

FOREIGN PATENT DOCUMENTS
EP   1 884 778 B1   2/2009
JP   2003-505678 A  2/2003

OTHER PUBLICATIONS

PCT/ISA/237 Written Opinion for PCT/JP2006/323302.*
Kawasaki, "Effects of Platelet Agonists on Thromboelastogram in the Presence of Heparin or Argatroban," American Society of Anesthesiologists Annual Meeting Abstracts, 2003, A-162.
Kawasaki, "The effects of vasoactive agents, platelet agonists and anticoagulation on thrombelastography," 2007 The Authors Journal compilation, 2007 Acta Anaesthesiol Scand.
Winter, Peter M., M.D. and Kang, Yoo Goo, M.D., "Hepatic Transplantation—Anesthetic and Perioperative Management", 1986, 14 pages (pp. 150-173), Praeger Publishers, New York, NY.

* cited by examiner

*Primary Examiner* — Maureen M Wallenhorst
(74) *Attorney, Agent, or Firm* — Schwabe, Williamson & Wyatt, P.C.

(57) ABSTRACT

The present invention provides a method for testing quickly and easily the manner in which an antithrombotic agent inhibits the acceleration of blood coagulation when a platelet agonist causes acceleration of blood coagulation. The invention is a test method wherein a system in which an anticoagulant is added to a portion of blood sampled from a patient being administered an antithrombotic agent (X system blood), and a system in which an anticoagulant and adenosine diphosphate or collagen are added to a portion of the abovementioned blood (Y system blood) are simultaneously measured by thromboelastograph; and the efficacy of the antithrombotic agent is assessed by comparing the R values of the X system blood and the Y system blood. If the R value of the Y system blood is not found to differ significantly from the R value of the X system blood, the drug is judged to be working. Adenosine diphosphate and collagen can be used as the anticoagulant. The present invention provides a heretofore unknown method for easily assessing the efficacy of an antithrombotic agent.

12 Claims, 1 Drawing Sheet

METHOD FOR TESTING EFFICACY OF ANTITHROMBOTIC AGENT

TECHNICAL FIELD

The present invention relates to a method for testing the efficacy of an antithrombotic agent, and more particularly relates to a test method for quickly and easily assessing the efficacy of an antithrombotic agent being administered therapeutically.

BACKGROUND ART

Thromboembolism is a condition in which the blood has become solidified within the heart or a blood vessel. When the blood is stopped by a thromboembolism, a lesion develops in the area nourished by that blood vessel. An antithrombotic agent is necessary to prevent thromboembolism because a thromboembolism can be fatal.

As regards the assessment of the efficacy of antithrombotic agents and antiplatelet agents, it is inherently difficult to assess the efficacy of an antiplatelet agent owing to the presence of a strong platelet agonist called thrombin in the blood. There is in fact no effective means of assessment.

The potentiation of platelet activity was considered as a cause of thromboembolism, but there are no data to be found that clearly show clot formation to be speeded up when platelet activity is abnormally accelerated. From this viewpoint, there are data on the measurement of the degree of clot formation obtained using a thromboelastograph by adding adenosine diphosphate (ADP (final concentration 8.3 μM)) or collagen (Col: final concentration 10 μg/mL), which are platelet agonists, to whole blood (Non-patent Reference 1). The results are shown in Table 1. The control in Table 1 means blood itself without ADP, collagen, or the like added. The data in Table 1 are stated as the mean±standard deviation. R and K are thromboelastograph parameters. R is the time it takes for fibrin to be formed. K is the time it takes a clot to be formed.

TABLE 1

|     |         | R         | K         | R + K     | M A        |
|-----|---------|-----------|-----------|-----------|------------|
| ADP | control | 5.9 ± 1.7 | 2.4 ± 0.4 | 8.3 ± 1.9 | 58.5 ± 1.8 |
|     | 8.3 μM/L| 5.0 ± 1.0 | 3.1 ± 0.6 | 8.1 ± 1.6 | 57.9 ± 2.6 |
| Col.| control | 6.4 ± 2.6 | 2.6 ± 0.6 | 9.0 ± 2.9 | 57.3 ± 3.6 |
|     | 10 μg/mL| 5.3 ± 1.4 | 2.5 ± 0.5 | 7.8 ± 1.5 | 57.9 ± 3.9 |

The results in Table 1 indicate that R shortens significantly when ADP or collagen is added, but that K lengthens significantly when ADP is added, and shows no significant difference when collagen is added, and that R+K shows no significant difference when ADP is added, and shortens significantly when collagen is added. Therefore, clot formation speeds up when platelet aggregation is stimulated by collagen, and fibrin formation speeds up but clot formation slows down when platelet aggregation is stimulated by ADP, and no difference in clot formation is shown as a result. The amounts of platelet agonists such as adenosine diphosphate and collagen added in Table 1 are twice or more the maximum clinical doses to induce platelet activity. This amount is the amount that usually immediately coagulates the entire quantity of platelets. Despite this, the results in Table 1 simultaneously show that even addition of a concentration of platelet agonist twice or more the maximum clinical dose to induce platelet activity causes only slight acceleration of clot formation or causes no clear acceleration of clot formation.

The reason for this is believed to be that the thrombin present in the blood is itself an extremely potent platelet agonist and inhibits the effects of the other platelet agonists ADP and collagen. In Non-patent Reference 2, an antithrombin agent (heparin or argatroban) is added to slightly weaken the power of the thrombin in the blood. The platelets are then stimulated by adding ADP or collagen in the same final concentrations as in Table 1, and the extent of clot formation is measured on the thromboelastograph. The measurement results are shown in Table 2.

TABLE 2

|                    | R           | K          | A N G       |
|--------------------|-------------|------------|-------------|
| control            | 9.6 ± 3.7   | 2.8 ± 0.8  | 72.7 ± 5.8  |
| Hep(0.1 U/mL)      | 26.4 ± 10.6 | 11.4 ± 6.2 | 39.1 ± 13.9 |
| Hep + Col(10 μg/mL)| 19.2 ± 7.1  | 8.5 ± 4.6  | 45.4 ± 13.3 |
| Hep + ADP(8.3 μM/L)| 16.8 ± 8.1  | 7.4 ± 3.5  | 43.7 ± 13.2 |
| control            | 7.6 ± 2.4   | 2.2 ± 0.7  | 76.8 ± 3.7  |
| ARG(0.3 μg/mL)     | 29.8 ± 11.5 | 9.8 ± 5.1  | 44.5 ± 14.6 |
| ARG + Col(10 μg/mL)| 21.6 ± 5.6  | 6.3 ± 2.4  | 52.5 ± 10.8 |
| ARG + ADP(8.3 μM/L)| 20.6 ± 2.9  | 6.2 ± 1.7  | 53.3 ± 9.1  |

R and K lengthen when heparin or argatroban is added, and R and K clearly shorten when a platelet activator (ADP or collagen) is added. ANG, which represents the rapidity of clot formation, appears to tend to be increased by the platelet activators. This result clearly shows that the acceleration of platelet aggregation by the addition of the antithrombin agent heparin or argatroban can accelerate clot formation.

Non-patent Reference 1: American Society of Anesthesiologists (ASA) meeting abstract A-534 2002

Non-patent Reference 2: American Society of Anesthesiologists (ASA) meeting abstract A-1 62 2003

DISCLOSURE OF THE INVENTION

Problems to Be Solved by the Invention

The present inventors believed that the measurement of the degree of clot formation on the thromboelastograph in the presence of heparin or argatroban might be applicable as a method of assaying and testing how an antithrombotic agent inhibits the acceleration of blood coagulation when a platelet agonist is the cause of accelerated blood coagulation, and the present invention was perfected.

Specifically, an object of the present invention is to provide a method for testing quickly and easily how an antithrombotic agent inhibits the acceleration of blood coagulation when a platelet agonist is the cause of the acceleration of blood coagulation. There were no methods of assaying and testing how an antithrombotic agent inhibits the acceleration of blood coagulation in the past due to the complex interrelationship of factors because ordinary blood contains platelet agonists.

Means Used to Solve the Above-Mentioned Problems

The essence of the present invention is a method for testing the efficacy of an antithrombotic agent wherein a system in which an anticoagulant is added to a portion of blood sampled from a patient being administered an antithrombotic agent (X system blood), and a system in which an anticoagulant and adenosine diphosphate or collagen are added to a portion of the abovementioned blood (Y system blood) are simultaneously measured by thromboelastograph; the R values of the X system blood and the Y system blood are measured; and the efficacy of the administered antithrombotic agent is assessed. Here, heparin or argatroban can preferably be used as the anticoagulant.

The X system blood and Y system blood used can have calcium chloride added. The X system blood used can also have physiological saline added.

The amount of adenosine diphosphate added to the sampled blood is preferably 8.3 µM or more. Similarly, the amount of collagen added is preferably 10 µg/mL or more.

The blood sampled from the patient being administered the antithrombotic agent may be treated by kaolin. Typical kaolin treatment involves placing the sampled blood in a kaolin-coated vial.

As was stated above, the essence of the present invention is a method for testing the efficacy of an antithrombotic agent wherein a system in which an anticoagulant is added to a portion of blood sampled from a patient being administered the antithrombotic agent (X system blood), and a system in which an anticoagulant and adenosine diphosphate or collagen are added to a portion of the abovementioned blood (Y system blood) are simultaneously measured by thromboelastograph; the R values of the X system blood and the Y system blood are compared; and the efficacy of the administered antithrombotic agent is assessed.

The procedure of this test method is described next. Blood is sampled from a patient who has been prescribed and is being administered an antithrombotic agent. Sodium citrate is usually used to prevent coagulation of the blood when sampling the blood. Calcium chloride treatment is performed to eliminate the effects of this sodium citrate on the thromboelastogram. The clotting factor activator kaolin can also be used (kaolin treatment) to avoid having measurement of the blood coagulation take a long time and to permit measurement in a relatively short time. Calcium chloride is added to the sampled blood as calcium chloride treatment. The sampled blood is generally placed in a vial coated with kaolin as kaolin treatment. A method of immersing the blood in a container that contains kaolin can also be used. When citric acid has been used during blood sampling, calcium chloride treatment is necessarily performed, although it is also possible for both kaolin treatment and calcium chloride treatment to be performed. After performing kaolin treatment and/or calcium chloride treatment, the anticoagulant and adenosine diphosphate or collagen are added and measurement is made by thromboelastograph.

Argatrobans and heparins can typically be used as anticoagulants. It is also possible to use antithrombin drugs typified by argatroban, concentrated antithrombin formulations, urokinases, heparin and low molecular heparins, natural and recombinant plasminogen activator (t-PA) formulations, platelet inhibitors, aspirin, GPIIb/IIIA inhibitor, PDE-III inhibitor (cilostazol), thienopyridines (clopidogrel), and the like.

Adenosine diphosphate or collagen is preferably used in a concentration twice or more the maximum clinical dose to induce platelet activity. Concretely speaking, adenosine diphosphate is added to make 8.3 µM or more. Similarly, collagen is added to make 10 µg/mL or more. Effective thromboelastograph measurement is not possible when the amount added is less than the aforementioned amount.

Effect of the Invention

The fact that there are anticoagulants that induce a state of accelerated blood coagulation in the presence of heparin, do not induce a state of accelerated blood coagulation in the presence of argatroban, but do not induce a state of accelerated blood coagulation in the presence of either heparin or argatroban makes it possible to test the efficacy of an antithrombotic agent quickly and easily. This test method can make it evident where the direction of more suitable treatment lies (such as the prescription of an antithrombotic agent).

BEST MODE FOR CARRYING OUT THE INVENTION

The present invention is described below based on embodiments. The thromboelastograph will be described first. A thromboelastograph is an apparatus that tracks the process of blood coagulation by the clot elasticity in whole blood. FIG. 1 shows a graph of the clot elasticity value on the ordinate, and the changes over time therein on the abscissa. The reaction time R representing the time when the range of the clot elasticity value reaches 2 mm, the coagulation time K representing the time when the range of the clot elasticity value reaches 20 mm, the maximum amplitude MA of the range of the clot elasticity values, the angle ANG formed by a tangent drawn on the graph of the changes in clot elasticity, and the like are obtained as numerical values based on the measurement chart, as shown in FIG. 1. The measurement procedure itself merely comprises placing the blood in a cuvette and beginning measurement. A C-TEG3000T machine made by Haemoscope of the United States was used as the thromboelastograph in the examples below.

The test method using the thromboelastograph will be described next in itemized form. 1) A thromboelastograph is used in measurement. The thromboelastograph used is one in which the measurement part has two or more channels, and the amount of fluid measured is 0.36 mL. 2) The blood of the patient being administered an antithrombotic agent is sampled by a blood sampling tube for coagulation testing. Citric acid is usually admixed in the blood sampling tube for coagulation testing so that coagulation does not begin. 3) 0.02 mL of 0.2 M calcium chloride and 0.32 mL of blood from the blood sampling tube are mixed with 0.01 mL of anticoagulant and 0.01 mL of physiological saline in the first measurement part (first channel) of the thromboelastograph. The calcium chloride neutralizes the citric acid admixed in the blood sampling tube, and coagulation begins. 4) 0.02 mL of 0.2 M calcium chloride and 0.32 mL of blood from the blood sampling tube are mixed with 0.01 mL of anticoagulant and 0.01 mL of adenosine diphosphate (ADP) or collagen in the second measurement part (second channel) of the thromboelastograph. The adenosine diphosphate (ADP) used here is 0.2 µmol of commercial reagent powder dissolved in 0.67 mL of physiological saline. Similarly, the collagen is 1 mg/mL stock solution diluted to a 36% solution by physiological saline. 5) The first channel and second channel are measured simultaneously by the thromboelastograph, and the R values measured on the thromboelastograph are compared. 6) When the R value of the second channel is significantly shorter than the R value of the first channel, the antithrombotic agent being administered can be judged to be ineffective. It is necessary in this case to strengthen the antithrombotic effect by measures such as increasing the dose or changing the antithrombotic agent being administered. The platelets in the second channel are believed to be readily activated by the ADP or collagen, and blood coagulation is accelerated. 7) When the R value of the second channel does not differ significantly from the R value of the first channel, the antithrombotic agent being administered is judged to be effective. It is believed in this case that the platelets in the second channel are not readily activated by the ADP or collagen, and blood coagulation is not accelerated.

Antithrombin agents typified by argatroban, concentrated antithrombin III formulations, urokinases, heparin and low molecular heparins, natural and recombinant plasminogen activator (t-PA) formulations, platelet inhibitors, aspirin, GPIIb/IIIa inhibitor, PDE-III inhibitor (cilostazol), thienopyridines (clopidogrel), and the like can be used as the anticoagulants in 3) and 4) above.

The anticoagulants used here include ADP in a concentration of 8.3 µM or higher, and collagen in a concentration of 10 µg/mL or higher. Below this concentration, the effect of thrombin remains and the R value measured lacks reliability. When the coagulants are used at or above the indicated concentrations, the measured R values constitute reliable data. Also, it sometimes takes a long time for the blood to begin to coagulate when the thromboelastograph is actually used. In such cases, the measurements can be conducted using a thromboelastograph on a test basis in the presence of a certain amount of an antithrombin agent (such as heparin or argatroban), and the time when the blood begins to coagulate can be confirmed. If it takes a long time for coagulation to begin, the appropriate amount of antithrombin agent to use can be decided by testing, such as reducing the amount of heparin or argatroban used.

Also, when measurement takes an extremely long time, kaolin treatment is carried out by immersing the blood from the blood sampling tube in kaolin (for approximately 2 minutes) or the like, and this blood is measured by thromboelastograph.

In the following examples and comparative examples, the addition of 0.02 mL of physiological saline of 0.2 M calcium chloride to the sampled blood and the addition of 0.02 mL of physiological saline to the system without ADP or collagen added are common to all examples and are omitted from the explanations of each example and comparative example.

Example 1

An example of the administration of aspirin as an antithrombotic agent will be described. First, 81 mg/day of aspirin was administered for three days. Blood sampled one hour after oral administration of 40.5 mg of aspirin thereafter was measured using a thromboelastograph. Specifically, thromboelastographic measurements were simultaneously carried out on the sampled blood itself, the same blood with 0.1 U/mL of heparin or 0.31 µg/mL of argatroban added, and blood obtained by adding 8.3 µM of ADP or 10 µg/mL of collagen to these. The measurement results are shown in Table 3.

TABLE 3

|  | R value |
| --- | --- |
| ASP(Control) | 6.4 ± 1.5 |
| ASP + Hep | 22.8 ± 7.5 |
| ASP + Hep + ADP | 14.9 ± 8.1 |
| ASP + Hep + Col | 14.2 ± 6.3 |
| ASP + ARG | 20.3 ± 3.5 |
| ASP + ARG + ADP | 13.8 ± 3.6 |
| ASP + ARG + Col | 12.9 ± 3.2 |

Also, 660 mg/day of aspirin was administered for three days, and the blood sampled one hour after oral administration of 330 mg thereafter was measured in the same manner by using a thromboelastograph. The measurement results are shown in Table 4.

TABLE 4

|  | R value |
| --- | --- |
| ASP(Control) | 6.67 ± 1.7 |
| ASP + Hep | 22.5 ± 8.4 |
| ASP + Hep + ADP | 21.9 ± 8.2 |
| ASP + Hep + Col | 21.4 ± 6.5 |
| ASP + ARG | 18.9 ± 3.5 |
| ASP + ARG + ADP | 18.7 ± 3.2 |
| ASP + ARG + Col | 18.5 ± 3.6 |

In administration of 81 mg/day of aspirin for three days (Table 3), the R value normally lengthened by heparin or argatroban is shortened by ADP and collagen. This dose is insufficient to function effectively, and must be increased. It was learned that when 660 mg/day of aspirin was administered for three days, the R value normally lengthened by heparin or argatroban was not shortened by ADP or collagen. This dose is understood to function adequately.

Example 2

An example of the administration of sulpyrine will be described next. First, Table 5 shows the results of a thromboelastograph measurement when no sulpyrine was administered. The measurement was the same as in Example 1. Blood with 0.1 U/mL of heparin or 0.31 µg/mL of argatroban added and blood with 8.3 µM of ADP or 10 µg/mL of collagen added to these were measured simultaneously by using a thromboelastograph.

TABLE 5

|  | R value |
| --- | --- |
| Control | 6.3 ± 2.4 |
| Hep | 26.4 ± 10.6 |
| Hep + ADP | 16.8 ± 8.1 |
| Hep + Col | 17.2 ± 7.8 |
| ARG | 29.8 ± 9.5 |
| ARG + ADP | 20.6 ± 2.9 |
| ARG + Col | 19.6 ± 5.6 |

Blood sampled one hour after intramuscular injection of 250 mg of sulpyrine with 0.1 U/mL of heparin or 0.31 µg/mL of argatroban added, and blood with 8.3 µM of ADP or 10 µg/mL of collagen added to these were measured simultaneously by using a thromboelastograph. The measurement results are shown in Table 6. When sulpyrine is not administered, the R value normally lengthened by heparin or argatroban is shortened by ADP and collagen. It was learned that when 250 mg of sulpyrine was injected intramuscularly, however, the R value normally lengthened by heparin or argatroban was not shortened by ADP or collagen. It is understood from these results that administration of 250 mg of sulpyrine functions adequately.

TABLE 6

|  | R value |
| --- | --- |
| Sulp(Control) | 6.9 ± 2.1 |
| Sulp + Hep | 24.0 ± 6.7 |
| Sulp + Hep + ADP | 23.4 ± 5.7 |
| Sulp + Hep + Col | 23.9 ± 6.9 |
| Sulp + ARG | 26.5 ± 2.1 |
| Sulp + ARG + ADP | 25.8 ± 1.9 |
| Sulp + ARG + Col | 26.3 ± 2.7 |

Example 3

An example of the administration of Pletaal will be described next. First, as in Example 2, Table 7 shows the results of thromboelastograph measurements when no Pletaal was administered. The amounts of heparin, argatroban, ADP, and collagen added were the same as in Example 2.

TABLE 7

|  | R value |
| --- | --- |
| Control | 6.8 ± 2.4 |
| Hep | 28.6 ± 9.5 |
| Hep + ADP | 14.8 ± 8.4 |
| Hep + Col | 15.2 ± 7.6 |
| ARG | 29.7 ± 10.5 |
| ARG + ADP | 19.5 ± 2.9 |
| ARG + Col | 20.8 ± 6.4 |

Blood sampled one hour after oral administration of 100 mg following administration of 200 mg/day of Pletaal for five days was measured using a thromboelastograph in the same manner as in Example 1. The measurement results are shown in Table 8. Blood with 0.04 U/mL of heparin or 0.06 µg/mL of argatroban added, and blood with 8.3 µM of ADP or 10 µg/mL of collagen added to these were measured simultaneously by using a thromboelastograph. When Pletaal was not administered, the R value normally lengthened by heparin or argatroban was markedly shortened by the addition of ADP and collagen. Pletaal administration, however, is understood to cause the R value normally lengthened by heparin and argatroban to not be shortened by ADP or collagen. It is understood from these results that 200 mg/day of Pletaal functions adequately.

TABLE 8

|  | R value |
| --- | --- |
| Cil( Control) | 14.5 ± 3.7 |
| Cil + Hep | 34.0 ± 15.1 |
| Cil + Hep + ADP | 36.1 ± 14.8 |
| Cil + Hep + Col | 36.4 ± 13.0 |
| Cil + ARG | 29.1 ± 3.8 |
| Cil + ARG + ADP | 30.3 ± 3.9 |
| Cil + ARG + Col | 31.1 ± 3.6 |

When Pletaal was administered, the amount of heparin was set at 0.04 U/mL, and the amount of argatroban was set at 0.06 µg/mL. These amounts are 4/5 and 1/5, respectively, of the 0.1 U/mL of heparin and 0.31 µg/mL of argatroban used in Examples 1 and 2. When Pletaal was administered as an antithrombotic agent, the blood did not begin to coagulate even after more than 3 hours when 0.1 U/mL of heparin and 0.31 µg/mL of argatroban were used. In other words, the R value could not be determined on the thromboelastograph. Therefore, to shorten the time it takes the blood to start to coagulate, the amounts of heparin and argatroban used were decreased as above. It is necessary to adjust the amounts of heparin and argatroban used in this way while monitoring the time it takes blood coagulation to begin. The amounts of ADP and collagen were unchanged even in this case.

Comparative Example

As a comparative example, blood obtained when no thrombotic agent (*1) had been administered was measured by thromboelastograph. Specifically, systems of heparin, ADP, and collagen added to blood that contained no thrombotic agent and, similarly, systems of argatroban, ADP, and collagen added to blood that contained no thrombotic agent were measured using a thromboelastograph. The measurement results are shown in Table 9.

TABLE 9

|  | R value |
| --- | --- |
| Control | 7.8 ± 3.7 |
| Hep | 26.4 ± 10.6 |
| Hep + ADP | 16.8 ± 8.1 |
| Hep + Col | 19.2 ± 7.1 |
| Control | 7.6 ± 2.4 |
| ARG | 29.8 ± 11.5 |
| ARG + ADP | 20.6 ± 2.9 |
| ARG + Col | 21.6 ± 5.6 |

The R value lengthens when an anticoagulant (heparin or argatroban) is added to blood in a case in which the blood coagulation function is normal and no antithrombotic agent has been administered, and the lengthened R value always shortens significantly when ADP or collagen is added. This is because normal platelets are stimulated by ADP or collagen, resulting in rapid platelet aggregation and accelerated clot formation. These data are fundamentally the same as those stated in Non-patent Reference 1.

Here, when an antithrombotic agent is administered and ADP or collagen is added after an anticoagulant is added in the same manner, the drug effect of the antithrombotic agent administered is judged to be inadequate when the R value shortens significantly, rapid platelet aggregation occurs, and clot formation is accelerated. It is believed that when the R value does not decrease, the agent works satisfactorily so that abnormal platelet aggregation is inhibited, clot formation is not accelerated, and the platelets are not abnormally activated even when there are factors that may induce abnormal activation of the platelets.

As was described previously, the thrombi that cause myocardial infarction and cerebral infarction are composed of aggregated platelets that occur when some factor causes suddenly heightened platelet activity. The platelets are readily activated, triggering platelet aggregation. Blood coagulation is accelerated and a clot forms. This is believed to block a coronary artery, leading to myocardial infarction, or to block a cerebral artery, leading to cerebral infarction. When testing the effect of an antithrombotic agent, one might believe simply that the effect of the antithrombotic agent can be tested easily by comparing the process of coagulation of blood from a patient who is administered the antithrombotic that is devoid of any additives and the same blood to which adenosine diphosphate (ADP) or collagen has been added. In practice, however, there is virtually no difference between the two if one compares the process of coagulation of blood devoid of any additives and blood with adenosine diphosphate (ADP) or collagen added. The main cause of this is the thrombin present in the patients blood. This thrombin is a very powerful platelet aggregating agent. The effect of ADP or collagen, which is a platelet aggregating agent that is much weaker than thrombin, tends to be suppressed by thrombin. When the thrombin is powerful, strong platelet aggregation is not triggered even if platelet aggregation has a tendency to be readily induced by ADP or collagen. This is believed to be the reason that no difference is found in the two measurements.

More than twice the maximum clinical dose of ADP or collagen to induce platelet activity is added in the present invention to rapidly promote platelet activity and induce aggregation, accelerate thrombi and coagulation, and artificially create a clot. The anticoagulant (argatroban or heparin) used in the present invention is used to suppress the effect of this thrombin. When the platelets are readily activated by ADP or collagen while thrombin is suppressed by an anticoagulant, powerful platelet aggregation will be triggered when the antithrombotic agent is not effective, and coagulation will be accelerated. When the antithrombotic agent is effective, strong platelet activation will not be induced even if ADP or collagen causes strong platelet aggregation, and the blood does not coagulate. This difference is evident when an anticoagulant is used. The present invention thus makes it possible to assess the efficacy of an antithrombotic agent.

As a test method to assess the efficacy of an antithrombotic agent, the state of acceleration of blood coagulation is checked by thromboelastograph in a system in which the agent and a platelet agonist are added in the presence of heparin, and in a system in which the agent and a platelet agonist are added in the presence of argatroban.

INDUSTRIAL APPLICABILITY

The present invention is a method for easily testing the efficacy of an antithrombotic agent. There was no method of testing the efficacy of an antithrombotic agent in the past. The present invention opens the way to testing the efficacy of antithrombotic agents for the first time. The present invention greatly contributes to the medical science, medical care, and pharmaceutical fields.

DESCRIPTION OF ALPHANUMERICAL SYMBOLS

Figure 1:
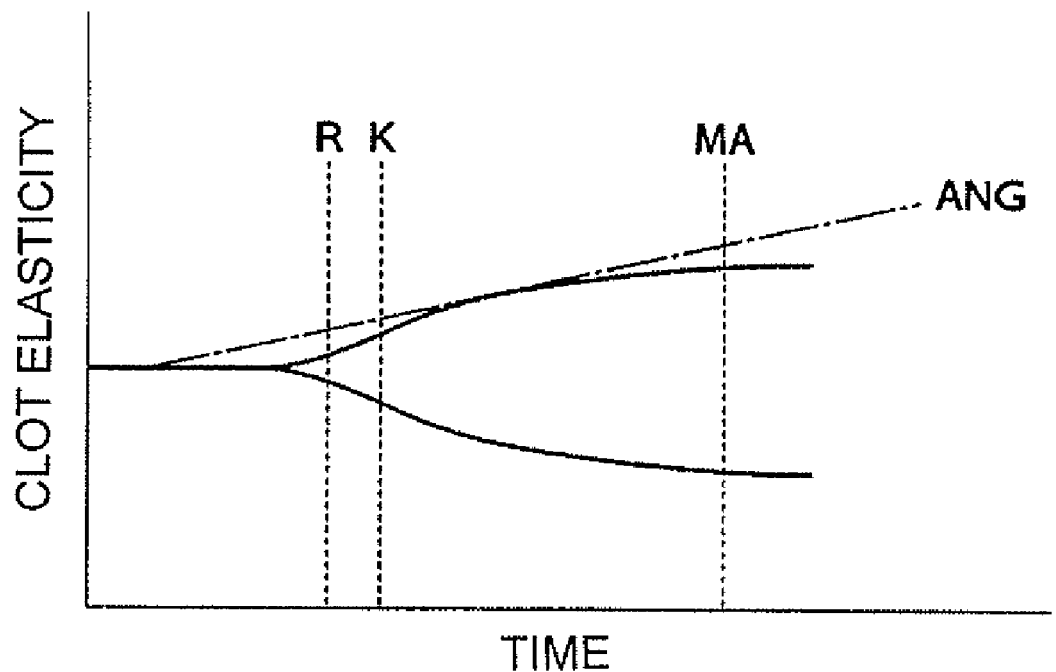
FIG. 1 is a diagram that describes thromboelastographic measurements.

R Time when the range of the clot elasticity value reaches 2 mm
K Time when the range of the clot elasticity value reaches 20 mm
MA Maximum amplitude MA of the range of the clot elasticity values
ANG Angle formed by a tangent drawn on a graph of changes in clot elasticity

The invention claimed is:

1. A method comprising:
preparing a first system blood (X system blood) in which an anticoagulant is added to a portion of blood sampled from a patient having been administered with an antithrombotic agent;
preparing a second system blood (Y system blood) in which the anticoagulant and a quantity of adenosine-diphosphate or collagen are added to a portion of the sampled blood, thereby making an R value of the Y system blood (Ry value) to be responsive, under thromboelastography, to changes in effectiveness of the antithrombotic agent;
measuring, by thromboelastography, an R value of the X system blood (Rx value) and the Ry value; and
comparing the Rx value with the Ry value to assess efficacy of the antithrombotic agent.

2. The method according to claim 1, wherein the anticoagulant is heparin or argatroban.

3. The method according to claim 2, wherein calcium chloride is also added to the X system blood and the Y system blood.

4. The method according to claim 3, wherein physiological saline is also added to the X system blood.

5. The method according to claim 2, wherein the amount of the adenosine diphosphate added is 8.3 μM or more and the amount of collagen added is 10 μg/mL or more.

6. The method according to claim 2, wherein the blood sampled from the patient having been administered with the antithrombotic agent is treated by kaolin.

7. The method according to claim 6, wherein the kaolin treatment comprises placing the blood in a kaolin-coated vial.

8. The method according to claim 1, wherein calcium chloride is also added to the X system blood and the Y system blood.

9. The method according to claim 8, wherein physiological saline is also added to the X system blood.

10. The method according to claim 1, wherein the amount of the adenosine diphosphate added is 8.3 μM or more, and the amount of collagen added is 10 μg/mL or more.

11. The method according to claim 1, wherein the blood sampled from the patient having been administered with the antithrombotic agent is treated by kaolin.

12. The method according to claim 11, wherein the kaolin treatment comprises placing the blood in a kaolin-coated vial.

* * * * *